United States Patent
Ishikawa et al.

(10) Patent No.: US 11,961,204 B2
(45) Date of Patent: Apr. 16, 2024

(54) STATE VISUALIZATION DEVICE, STATE VISUALIZATION METHOD, AND STATE VISUALIZATION PROGRAM

(71) Applicant: RIKEN, Saitama (JP)

(72) Inventors: Tetsuo Ishikawa, Saitama (JP); Eiryo Kawakami, Saitama (JP)

(73) Assignee: RIKEN, Saitama (JP)

( * ) Notice: Subject to any disclaimer, the term of this patent is extended or adjusted under 35 U.S.C. 154(b) by 302 days.

(21) Appl. No.: 17/329,529

(22) Filed: May 25, 2021

(65) Prior Publication Data

US 2021/0279838 A1 Sep. 9, 2021

Related U.S. Application Data

(63) Continuation of application No. PCT/JP2019/046338, filed on Nov. 27, 2019.

(30) Foreign Application Priority Data

Nov. 27, 2018 (JP) .................................. 2018-221449
Dec. 14, 2018 (JP) .................................. 2018-234464

(51) Int. Cl.
  *G06T 3/06* (2024.01)
  *G06T 3/4007* (2024.01)
  *G06T 7/70* (2017.01)
(52) U.S. Cl.
  CPC .............. *G06T 3/06* (2024.01); *G06T 3/4007* (2013.01); *G06T 7/70* (2017.01)

(58) Field of Classification Search
  CPC ........ G06T 3/0031; G06T 7/70; G06T 3/4007
  See application file for complete search history.

(56) References Cited

U.S. PATENT DOCUMENTS

2008/0234943 A1\* 9/2008 Ray ........................ G16H 50/20
600/300

FOREIGN PATENT DOCUMENTS

JP 2009-037588 2/2009

OTHER PUBLICATIONS

Ezaki et al., Multidimensional Time Series Analysis Tools Announced, Jul. 2017, online, retrieved: Jun. 14, 2023 https://tezk.hatenablog.com/entry/2017/07/10/144941 (Year: 2017).\*

(Continued)

*Primary Examiner* — Wednel Cadeau
(74) *Attorney, Agent, or Firm* — GREENBLUM & BERNSTEIN, P.L.C.

(57) ABSTRACT

A novel technique is provided that analyzes the state of life using multivariate data relating to life. A state visualization device includes: a coarse-graining portion configured to perform coarse-graining on values corresponding to a plurality of items included in sample data; a model creation portion configured to obtain, using binarized values, a mathematical model for calculating energies each fitting a frequency of occurrence of a state represented by a combination of values corresponding to the items; a graph creation portion configured to create a graph in which the state is placed in two-dimensional space; and an interpolation processing portion configured to create a landscape image by smoothing and interpolating a discrete graph.

6 Claims, 15 Drawing Sheets

(56) References Cited

OTHER PUBLICATIONS

Watanabe et al., Energy Landscapes of Resting-State Brain Networks, Feb. 2014, Frontiers in NeuralInformatics. (Year: 2014).*
Written Opinion of the International Searching Authority (ISA) dated Feb. 10, 2020 issued in PCT/JP2019/046338 along with an English translation.
Jianyun Chai et al., "Contour Interpolation and Smooth Surface Reconstruction Using Partial Differential Equations.", Transactions of the Information Processing Society of Japan, Mar. 15, 2000, vol. 41, No. 3, pp. 733-741, ISSN: 0387-5806, p. 733, right column, line 4 to p. 734, left column, line 22, p. 736, right column, line 24 to p. 740, right column, line 14 (see the English translation of the Written Opinion of the ISA for disclosure of relevance).
International Search Report issued in International Patent Application No. PCT/JP2019/046338, dated Feb. 10, 2020, along with an English translation thereof.
Takahiro Ezaki, "Multidimensional Time Series Analysis Tool Announced.", [online], Jul. 10, 2017, all [retrieved: Feb. 3, 2020], Internet: <htto://tezk.hatenablog.com/entry/2017/07/10/144941> lines 10-45, 51-61, 69-96 (see the English translation of the Written Opinion of the ISA for disclosure of relevance).
Thomas M. J. Fruchterman, Edward M. Reingold, "Graph drawing by force-directed placement.", Software—Practice and Experience, vol. 21(11), Nov. 1991, p. 1129-1164.
Hiroshi Akima, "Algorithm 760: Rectangular-Grid-Data Sur face Fitting that Has the Accuracy of a Bicubic Polynomial," ACM Transactions on Mathematical Software, Sep. 1996, vol. 22, No. 3, p. 357-361.
Kruskal, J. B., "Multidimensional scaling by optimizing goodness of fit to a nonmetric hypothesis." Psychometrika, Mar. 1964, vol. 29, Issue 1, pp. 1-27.
T. Ezaki, T. Watanabe, M. Ohzeki, and N. Masuda, "Energy landscape analysis of neuroimaging data", Philosophical transactions of the royal society A, May 15, 2017, vol. 375, Issue 2096.

\* cited by examiner

STATE VISUALIZATION DEVICE, STATE VISUALIZATION METHOD, AND STATE VISUALIZATION PROGRAM

CROSS-REFERENCE TO RELATED APPLICATION

This application is a continuation application of International Application No. PCT/JP2019/046338, filed Nov. 27, 2019, which claims priorities to Japanese Patent Application No. 2018-221449, filed on Nov. 27, 2018 and Japanese Patent Application No. 2018-234464, filed on Dec. 14, 2018. The contents of these applications are incorporated herein by reference in their entirety.

FIELD

The present technique relates to a state visualization device, a state visualization method, and a state visualization program.

BACKGROUND

Various measurement data obtained by monitoring the states of living organisms have been accumulated, including multivariate data of multiple items such as health care information. However, such data are occasionally not fully or effectively used for research.

Examples of techniques that are used to represent the relationship of multivariate data include a graph drawing technique that uses a force-directed model to place discrete states in lower-dimensional space (see, for example, Fruchterman, T. M.; Reingold, E. M. Graph drawing by force-directed placement, SOFTWARE-PRACTICE AND EXPERIENCE, VOL. 21(1 1), November 1991, pp 1129-1164), a technique that draws smooth curved surfaces by continuously interpolating discrete multivariate functions (see, for example, Akima, H. Algorithm 760: Rectangular-Grid-Data Surface Fitting that Has the Accuracy of a Bicubic Polynomial, ACM Transactions on Mathematical Software, September 1996, vol. 22, No. 3, pp 357-361), and a technique of projecting data in lower-dimensional space while maintaining the relationship of similarities between samples as much as possible (see, for example, Kruskal, J. B. Multidimensional scaling by optimizing goodness of fit to a nonmetric hypothesis, Psychometrika, March 1964, Volume 29, Issue 1, pp 1-27). The energy landscape analysis is a technique that uses an index called energy to study the stability of multivariate data and analyzes the energies of different states as a landscape. Techniques have been proposed that apply this energy landscape analysis to biological phenomena, such as multivariate time-series data of functional magnetic resonance imaging (fMRI) (see, for example, Ezaki, T.; Watanabe, T.; Ohzeki, M.; Masuda, N. Energy landscape analysis of neuroimaging data, Philosophical transactions of the royal society A, May 15, 2017, Volume 375, issue 2096).

SUMMARY

Biological data, including clinical and health data, lifelogs such as exercise amount, and animal behaviors, may be measured at irregular intervals, and the number of measurements may vary. On the other hand, such data involves a wide range of measurement items. It is difficult to perform statistical analysis on high-dimensional data that is not large in amount and measured at irregular intervals.

It is an objective of the present invention to provide a novel technique of analyzing the state of life using multivariate data relating to life.

The state visualization device according to the present invention includes: a coarse-graining portion configured to perform coarse-graining on values corresponding to a plurality of items included in sample data; a model creation portion configured to obtain, using binarized values, a mathematical model for calculating energies each fitting a frequency of occurrence of a state represented by a combination of values corresponding to the items; and a graph creation portion configured to create a graph in which the state is placed in two-dimensional space.

This configuration creates a graph (energy landscape) while maintaining the correspondence with the original sample data, visualizing the stability of each state and the likelihood of transition between states. That is, by using multivariate data such as clinical data as the sample data, the configuration provides a novel technique of analyzing the states of patients. The coarse-graining may be performed such that one variate is represented by multi-digit binary values (bits), or each variate may be converted into a binary value.

The state visualization device may further include an interpolation processing portion that interpolates energies between the states to create an interpolated graph. In this manner, energies can be calculated also for the states other than those of the lattice points that are degenerate due to the coarse-graining.

The state visualization device may further include an evaluation processing portion that performs coarse-graining on the data of an evaluation target, for example by binarizing the data, to determine the position of the data in the image. This allows the position of the individual data of the evaluation target to be recognized as a position in the image.

When a path extends in the direction in which the energy decreases most rapidly (the direction of gradient descent) from a given location in the image, the path eventually reaches a local minimum, and this range is defined as an attraction region of the local minimum (basin). The attraction region of each local minimum and a predetermined attribute of the sample data that belongs to the region may be associated with each other and stored in a storage device. The evaluation processing portion may extract the attribute corresponding to the data of the evaluation target and output the attribute. For example, the presence or absence of onset of a given disease after the measurement of clinical data may be associated as an attribute with an attraction region. This allows for the recognition of the relationship between the position in the energy landscape and the risk of onset, and the relationship between the state that is likely to transition in the future and the risk of onset.

The evaluation processing portion may binarize the data of the evaluation target obtained at a plurality of time points, determine a plurality of positions of the data in the image, and superimpose and display a course of change, over time, of the positions in the image. This enables the visualization of the history of states and the state that is likely to transition in the future of the evaluation target.

The configurations described in the summary can be combined without departing from the objectives and technical ideas of the present invention. Additionally, the configurations described in the summary may be provided as a device such as a computer or a system including a plurality of devices, a method performed by a computer, or a program executed by a computer. The program can be executed on a network. A storage medium that stores the program may also be provided.

The present invention provides a novel technique of analyzing the state of life using multivariate data relating to life, such as clinical data.

DESCRIPTION OF EMBODIMENTS

Figure 1:
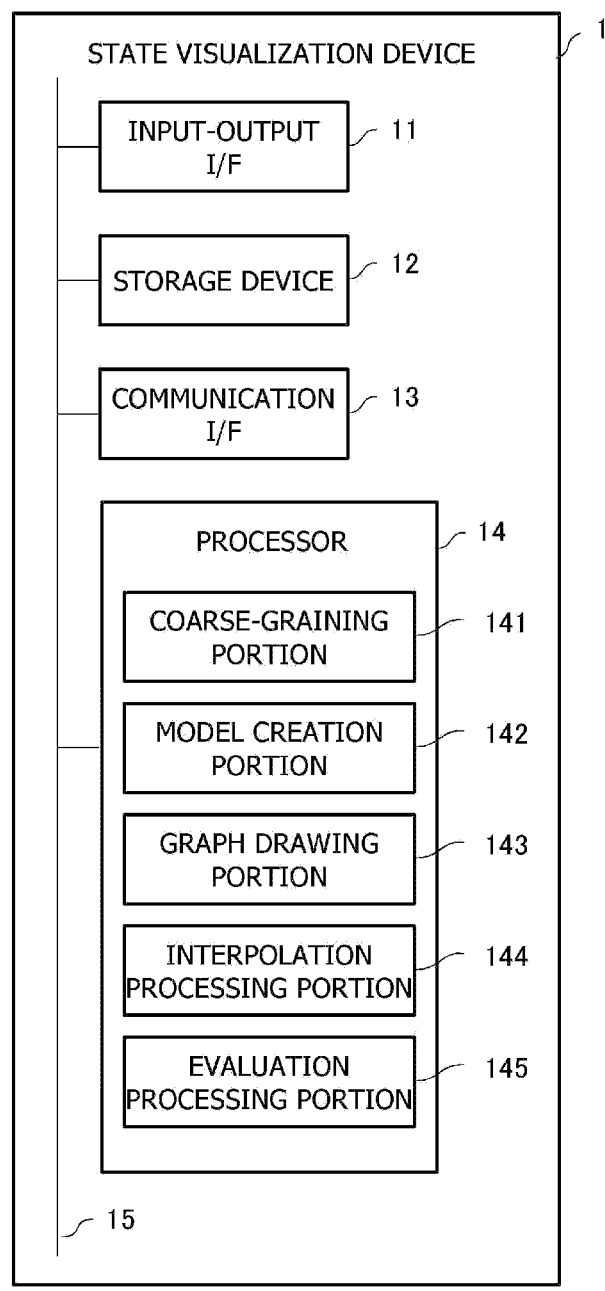
FIG. 1 is a block diagram showing an example of a state visualization device.

Referring to the drawings, embodiments of the present invention are now described. The following embodiments are illustrated by way of examples and not by way of lamination.

Functional Configuration of Device

FIG. 1 is a functional block diagram of a state visualization device according to an embodiment. A state visualization device 1 uses clinical data of a plurality of patients, including measurement results of a plurality of items of physical examinations, for example, to determine the stability of the health state of patients. The stability of health state of patients may be visualized for display. The present embodiment is an example that processes clinical data of patients, but the same device is also applicable to multivariate data relating to biological phenomena, such as other medical information, information obtained from various living organisms, daily observation values, and data obtained from various living organisms.

The state visualization device 1 according to the present embodiment may be a general computer and includes an input-output interface (I/F) 11, a storage device 12, a communication interface (I/F) 13, and a processor 14. A bus 15 connects these components.

The input-output I/F 11 may be a user interface such as a keyboard, a mouse, a display, or a touch panel. The state visualization device 1 receives user's operation via the input-output I/F 11, performs the processes described below, and displays the result. The storage device 12 may include a main storage device, such as a random access memory (RAM) or a read-only memory (ROM), and an auxiliary storage device (secondary storage), such as a hard-disk drive (HDD), solid state drive (SSD), or a flash memory. The main storage device temporarily stores the program read by the processor and the data to be processed, and secures the work area of the processor. The auxiliary storage device stores the program to be executed by the processor, clinical data, and other data. The communication I/F 13 may be a wired network card, for example, and communicates using a predetermined protocol. The processor 14 may be an arithmetic processing unit such as a central processing unit (CPU) and performs processes according to the present embodiment by executing a program.

FIG. 1 shows an example in which the processor 14 includes a functional block. Specifically, the processor 14 functions as a coarse-graining portion 141, a model creation portion 142, a graph drawing portion 143, an interpolation processing portion 144, and an evaluation processing portion 145. The coarse-graining portion 141, the model creation portion 142, the graph drawing portion 143, and the interpolation processing portion 144 create a model representing the likelihood of transition between states based on the frequency of occurrence of states representing clinical data of patients. The evaluation processing portion 145 evaluates the state of a patient of the evaluation target using the created model and the clinical data of this patient. Specifically, the coarse-graining portion 141 converts input data, which may be clinical data such as physical examination results, into discrete values by binarizing the data based on predetermined criteria, for example. The model creation portion 142 calculates a state stability index called energy by solving the inverse Ising problem using discrete values corresponding to the results of physical examination items, for example. The graph drawing portion 143 draws an energy landscape that represents, as a landscape, the adjacency relationship of the states represented by combinations of the discrete values described above and the obtained energy levels. The interpolation processing portion 144 interpolates energy levels between the states to draw a continuous energy landscape. The evaluation processing portion 145 uses the energy landscape and clinical data of a patient of evaluation target to output information indicating the current state of this patient and the likelihood of a future state change. At least a part of the functional configuration illustrated in FIG. 1 may be a cloud service provided by a server connected via a network.

Coarse-Graining

The present embodiment represents states using the Ising model. The Ising model is a microscopic spin interaction model introduced to describe the characteristics of magnets in physics and includes a plurality of lattice points, each taking two states. In the present embodiment, each lattice point corresponds to one of various biological information pieces, which may be obtained from medical information, physical examination items, sensors, questionnaires, and the like. For example, the combination of the states of the lattice points representing the measurement results of the physical examination items of a patient represents the heath state of the patient.

To represent a measurement result of a physical examination item with two states, the present embodiment binarizes each variable representing the measurement result of the physical examination item based on a predetermined criterion. That is, the measurement result is converted into 0 or 1 based on the inequality relation between a predetermined threshold and the measurement result or a value obtained by combining a plurality of measurement results. The binary values do not have to be 0 and 1 and may be −1 and +1 or other binary values. The results of physical examinations are thus applied to the Ising model by performing coarse-graining that binarizes variables as described above. Alternatively, data can be analyzed by performing coarse-graining that represents each variable with a combination of binary variables. For example, the data converted into multiple ordinal scales by coarse-graining may be represented by a multi-digit bit string so that the health state of a patient is represented by a combination of binary values.

Energy Landscape

The Ising model is represented by spin variables $\sigma_i$ and two types of parameters $h_i$ and $J_{ij}$. The subscripts i and j take values from 1 to N. N denotes the total number of spin variables. $\sigma_i$ represents the i-th spin variable and takes a value of either 0 or 1. $h_i$ represents how likely for $\sigma_i$ to become 1 as an independent spin. $h_i$ is a parameter called magnetic field in physics, and a spin to which a magnetic field is applied is more likely to face the direction of the magnetic field. $J_{ij}$ represents the likelihood that $\sigma_i$ and $\sigma_j$ take the same value (both 0 or both 1). That is, $J_{ij}$ represents the strength of coupling between the i-th spin and the j-th spin. In physics, when J is a positive value, the spins exhibit ferromagnetism and are stable when they are aligned in the same direction. When J is a negative value, the spins exhibit antiferromagnetism and tend to be in antiparallel alignment. Lists of $\sigma_i$ and $h_i$ are considered as vectors and represented by σ in bold and h in bold, respectively. A matrix having $J_{ij}$ as elements is represented by J in bold. The correlations between independent spins and pairs of spins (pairwise correlations) determine the stability of a specific spin configuration (arrangement of 0 and 1). The index representing this stability is called energy E. The energy E is given by the following Expression (1).

[Math. 1]

$$E(\sigma \mid h, J) = -\sum_{i=1}^{N} h_i \sigma_i - \frac{1}{2} \sum_{i=1}^{N} \sum_{\substack{j=1 \\ j \neq i}}^{N} J_{ij} \sigma_i \sigma_j \qquad (1)$$

The energy E represents that the stability of a specific state, that is, a spin configuration σ, is determined according to the parameters h and J. The lower the energy E, the more stable the state. When the energy E of a given state is determined, the probability of occurrence P of this state is determined by the Gibbs-Boltzmann distribution. A given state is observed in proportion to a function raised to the power of the energy E multiplied by −1. The probability of occurrence P is given by the following Expression (2).

[Math. 2]

$$P(\sigma \mid h, J) = \frac{\exp[-E(\sigma \mid h, J)]}{\sum_{\sigma'} \exp[-E(\sigma' \mid h, J)]} \qquad (2)$$

The denominator on the right side of Expression (2) is a normalization constant for setting the total probability to 1, and is a partition function in physics. In this partition function, σ' denotes the dummy variable for summing all states.

A lower energy increases the stability of the state, and a more stable state is observed more often and thus has a higher frequency of occurrence. Since each spin takes a value of 0 or 1 and there are N spins in total, the number of possible spin configurations (states) is 2N. In physics, the probability of occurrence of each spin configuration is obtained based on h and J that are already known (predetermined by experimental operation). In contrast, the present embodiment estimates h (bold) and J (bold) and determines the energy E of each state based on the frequency of occurrence of each spin configuration obtained by binarizing multivariables that are observed. That is, the present embodiment involves the inverse Ising problem.

To this end, h (bold) and J (bold) are estimated that best fit the frequency of occurrence of the observed spin configurations. Specifically, h (bold) and J (bold) are obtained using a known optimization method such that the empirical distribution of the state occurrence frequency matches the theoretical distribution for the expected value $<\sigma_i>$ of $\sigma_i$ and the expected value $<\sigma_i\sigma_j>$ of $\sigma_i\sigma_j$, which are the first-order and second-order expected values of the spin variables. As described above, the stability of discrete states can be expressed as a landscape.

Image Drawing

In the Ising model, the spins are flipped one at a time when the spin configuration changes. When one of the spins is flipped in a given state, this state is referred to as an adjacent state to the given state. N-variable data contains N spin variables, so that there are N positions where a spin can flip. That is, each state has N adjacent states. A state that has a lower energy than any of the adjacent N states (local minimum) is defined as a basin. A basin is stable because it has a lower energy than its surroundings. There may be a plurality of basins. Observing the spin configurations of basins provides the understanding of what types of combinations of levels of variables (for example, binarized physical examination results and test data) correspond to basins. Some basins have many patients with some diseases, while other basins do not. Some basins have one or more diseases that are likely to develop in the future, while other basins do not. The likelihood of transition between basins may be high with some basins and low with other basins.

Stepping in the direction of the lowest energy among the adjacent states from a given state will eventually lead to one of the basins. That is, for each of the states other than a basin, it is possible to know to which one of the adjacent states the state is likely to transition. By drawing arrows in the direction of lower energy and connecting the paths, an adjacency graph, which is a directed graph, is obtained. The present embodiment uses a graph drawing algorithm such as the Fruchterman-Reingold algorithm to determine the placement of vertices in two-dimensional space from the adjacency graph. The Fruchterman-Reingold algorithm is a force-directed graph drawing algorithm that determines the layout of vertices in which the forces of vertices are balanced and in equilibrium. Each vertex receives attractive forces from the vertices connected by edges and also receives repulsive forces from all the vertices other than itself. The obtained energies are allocated on the states thus drawn in two-dimensional space ((x, y) coordinates), so that the energy E is represented by a two-variable function E (x, y).

Interpolation Process

E(x, y) is defined by only $2^n$ points. Interpolating values to these points using a technique such as the Akima algorithm can obtain an energy landscape with smooth curved surfaces. The advantage of the Akima interpolation is that it limits fluctuations that may create artifacts (creating peaks and valleys that do not actually exist) around points where the values change steeply. The continuous energy landscape created in this manner may be displayed in different colors according to the level of energy, or may be drawn with contour lines indicating the energy levels. Alternatively, the energy landscape may be drawn in a virtual multidimensional space.

Process Flow

Figure 2:
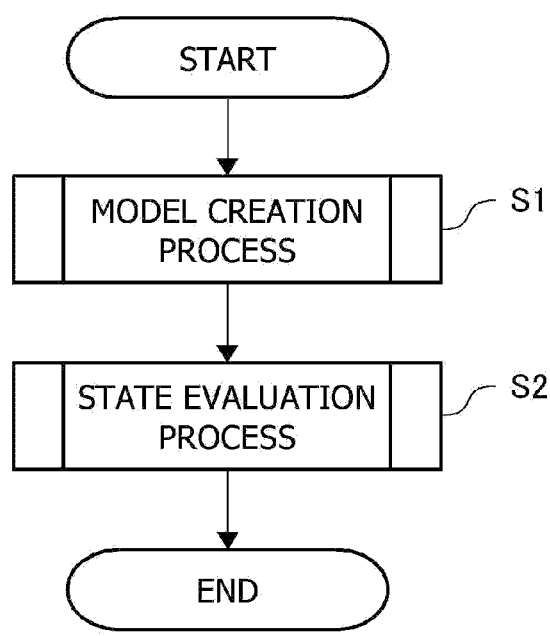
FIG. 2 is a process flow diagram showing an example of a process.

FIG. 2 is a process flow diagram showing an example of a process of the present embodiment. The coarse-graining portion 141, the model creation portion 142, the graph drawing portion 143, and the interpolation processing portion 144 of the state visualization device 1 perform the above processes to create a model of continuous energy landscape (FIG. 2, S1). This step may use clinical data of a plurality of patients, for example, to create an image showing the stability of states and the likelihood of transition between states.

Using data of a user of evaluation target, the evaluation processing portion 145 of the state visualization device 1 outputs information indicating the state of the user and the possibility of transition of the state in the future (FIG. 2, S2). This step uses the energy landscape created at S1 and the clinical data of the patient of evaluation target, for example, to show the state of this patient on the energy landscape.

Model Creation Process

Figure 3:
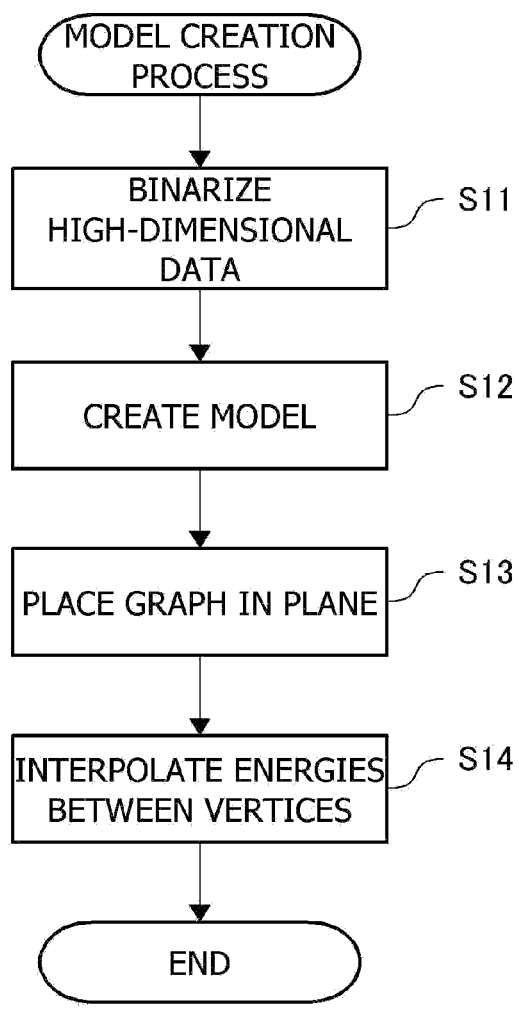
FIG. 3 is a process flow diagram showing an example of a model creation process.

FIG. 3 is a process flow diagram showing an example of the model creation process. The coarse-graining portion 141 of the state visualization device 1 binarizes high-dimensional data (FIG. 3, S11). In this step, the coarse-graining is performed as described above. The coarse-graining portion 141 may binarize each measurement value or combination of values of predetermined items in clinical data based on the equality relationship with a predetermined threshold. The predetermined threshold should be set such that the population is appropriately divided.

The model creation portion 142 of the state visualization device 1 creates a model for drawing an energy landscape using the binarized high-dimensional data (FIG. 3, S12). In this step, the model creation portion 142 adjusts the parameters based on the frequency of occurrence of each state represented by the binarized clinical data, for example, and creates a model for obtaining the energy E, which is an index representing the stability.

The graph drawing portion 143 of the state visualization device 1 draws a graph using the created model (FIG. 3, S13). This step uses a predetermined algorithm to draw the graph. For example, the nodes in the graph are placed such that fewer edges intersect in two-dimensional space. The graph may be drawn with fewer crossing edges by placing nodes connected by edges closer to one another, while keeping the balance so that the nodes are not too close together. This step may use the Fruchterman-Reingold algorithm, for example.

Then, the interpolation processing portion 144 of the state visualization device 1 interpolates values between the discrete basins in the created graph, thereby creating a continuous energy landscape (FIG. 3, S14). This step uses a predetermined algorithm for the interpolation between the energy levels of the vertices. The Akima algorithm may be used. The energy landscape may be represented as a two-dimensional image in which the difference in energy levels is distinguished with different colors.

State Evaluation Process

Figure 4:
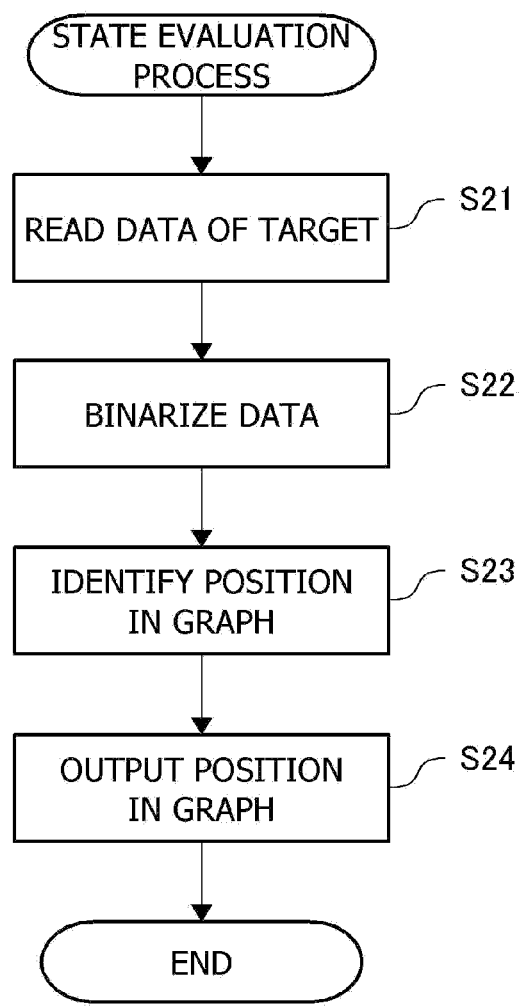
FIG. 4 is a process flow diagram showing an example of a state evaluation process.

FIG. 4 is a process flow diagram showing an example of the state evaluation process. The evaluation processing portion 145 of the state visualization device 1 reads the data of an evaluation target from the storage device 12 (FIG. 4, S21). This step reads out the values of the measurement items of the clinical data used to create the model described above.

The evaluation processing portion 145 then binarizes the read data (FIG. 4, S22). This step binarizes the data in the same manner as step S11 in FIG. 3.

The evaluation processing portion 145 also identifies the state of the evaluation target as a position in the energy landscape corresponding to the states represented by the binarized data (FIG. 4, S23), and outputs the position via the input-output I/F11, for example (FIG. 4, S24).

Advantages

The present embodiment allows for the understanding of the state of an individual and the identification of a state that is likely to transition in the future. Some states that are represented as basins in an energy landscape may have many patients who have a certain disease, while others do not. Some states are more likely to develop a disease, while others are not. The present embodiment can also visualize previously unknown states. By adjusting the physical examination items used for the spin variables of the Ising model, it is possible to create an energy landscape that includes a state where many patients have a specific disease, and also an energy landscape in which the states do not correlate with the morbidity of a specific disease. Furthermore, an image that shows a plurality of illnesses and health states can be created.

Example 1

A specific example of image creation is now described. An energy landscape representing the risk of developing diabetes was created using samples of clinical data. The clinical data included the following items. The values of the following items were binarized using the medians as the thresholds.

(1) Number of pregnancies
(2) 2-hour oral glucose tolerance test value
(3) Diastolic blood pressure
(4) Triceps skinfold thickness
(5) 2-hour serum insulin value
(6) BMI
(7) Diabetic family factor
(8) Age In addition, the relationship between the stability of states and the risk was evaluated using data on whether the samples developed diabetes within five years.

Figure 5:
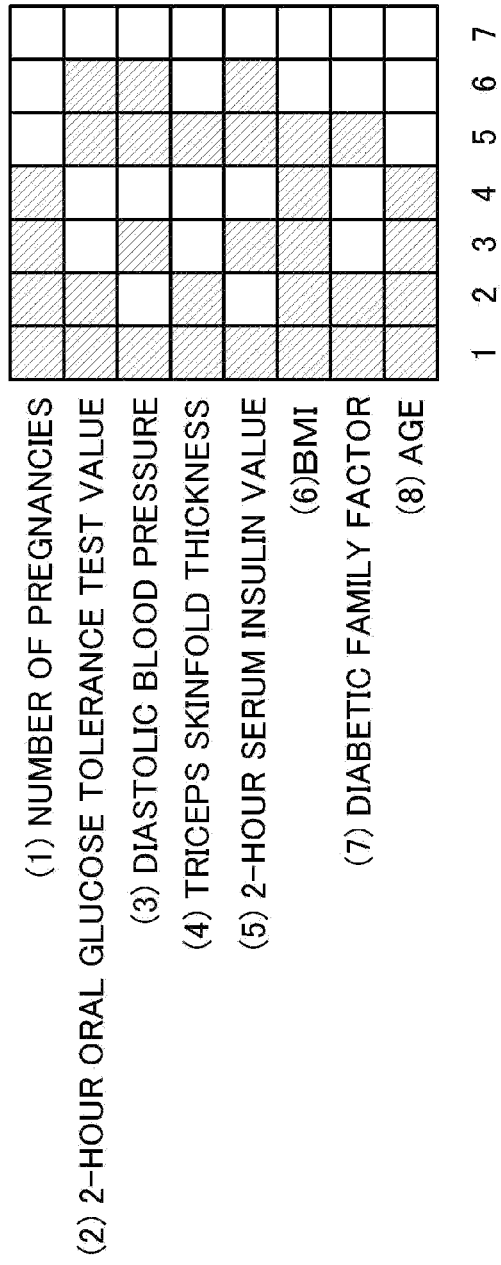
FIG. 5 is a diagram showing an example of combinations of binarized measurement values in stable states.
Figure 6:
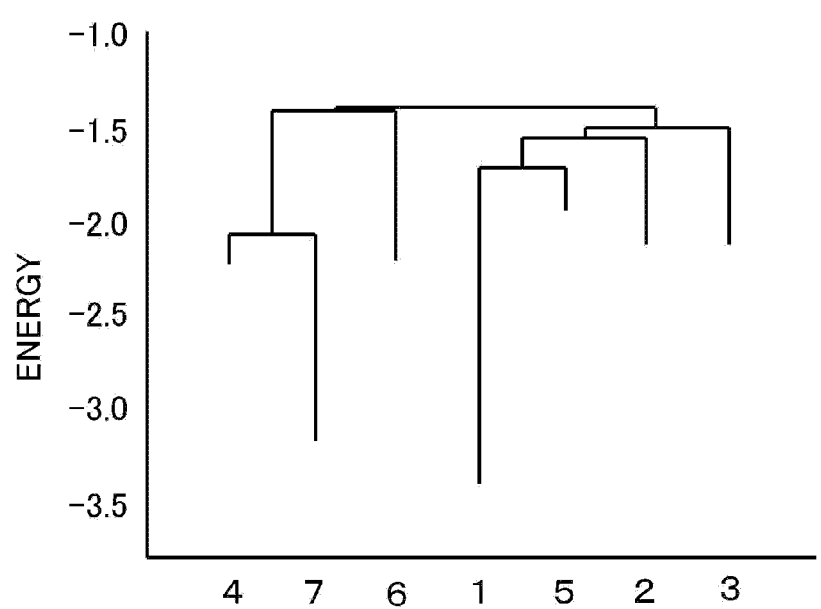
FIG. 6 is an example of a graph showing the levels of energy of basins.

Using combinations of the binarized measurement values of the items described above, the parameters $h_i$ and $J_{ij}$ of the Ising model that fit the occurrence frequencies of combinations were estimated to calculate energy E. Using the energy E thus obtained, the states where the energy E were lower than the surroundings were identified and determined as basins. FIG. 5 shows these basins 1 to 7 corresponding to combinations of binarized values. In the example of FIG. 5, the vertical axis represents the items, number of pregnancies, 2-hour oral glucose tolerance test value, diastolic blood pressure, triceps skinfold thickness, 2-hour serum insulin value, BMI, diabetic family factor, and age from the top. The color of each square indicates the value of the corresponding item. The hatched square represents 0, and the white square represents 1. The horizontal axis represents seven basins 1 to 7 that were identified as basins. For example, for Basin 1, the values of all items were 0. For Basin 2, only diastolic blood pressure and 2-hour serum insulin value had a value of 1. For Basin 3, 2-hour oral glucose tolerance test value, triceps skinfold thickness, and diabetic family factor had a value of 1. FIG. 6 is a graph showing the levels of energy of the basins. FIG. 6 is a disconnectivity graph that shows energy levels along the vertical axis and Basins 1 to 7 along the horizontal axis. The nodes at the distal ends of the branches represent basins. The node at a branch point represents the level of energy E at the lowest position along the ridgeline between basins. In addition to the basins, the energy levels can also be obtained from the values of h and J that are estimated based on the frequency of occurrence of the combinations of the values of the items described above.

Figure 7:
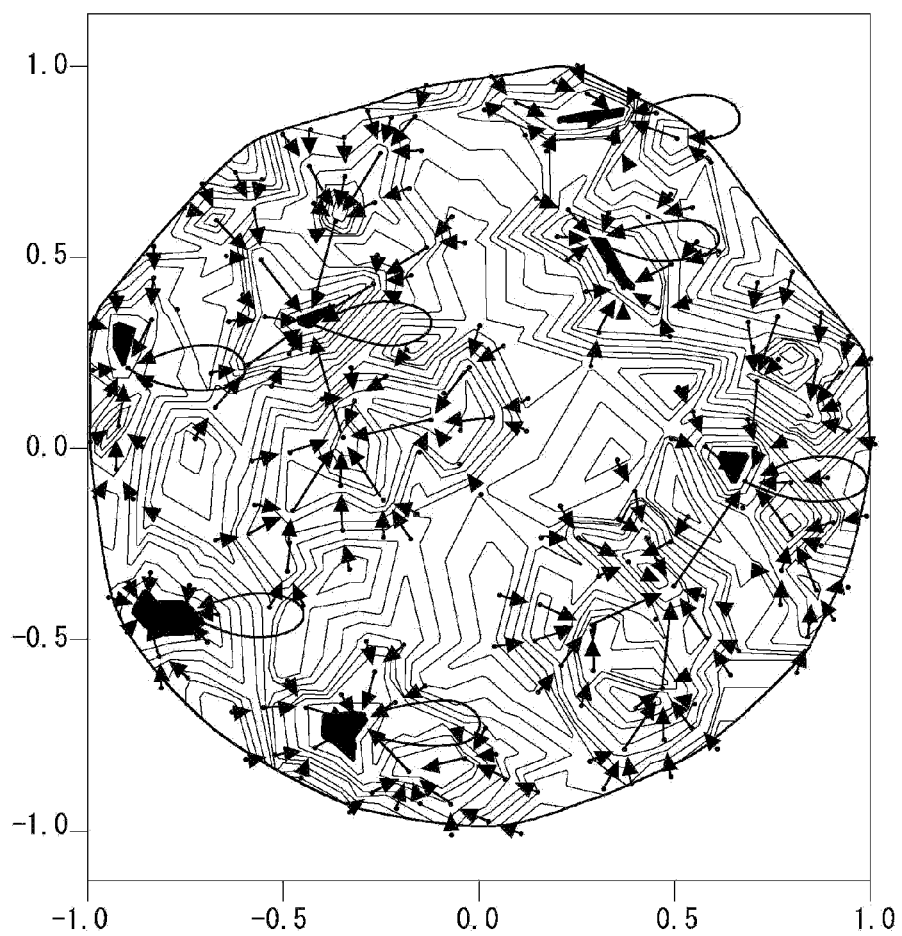
FIG. 7 is an example of an energy landscape showing the levels of energy of states placed in two-dimensional space.

Furthermore, the coordinates corresponding to each state were placed in two-dimensional space using the Fruchterman-Reingold algorithm, and an image was drawn by interpolating the levels of energy E between the coordinates using the Akima algorithm. FIG. 7 is an energy landscape in which the levels of energy E of states placed in two-dimensional space are represented by contour lines. Regions in black represent basins and their neighboring regions (valleys). Each arrow indicates a path extending in the direction of gradient descent from the corresponding location. That is, a location where arrows gather is a basin.

Figure 8:
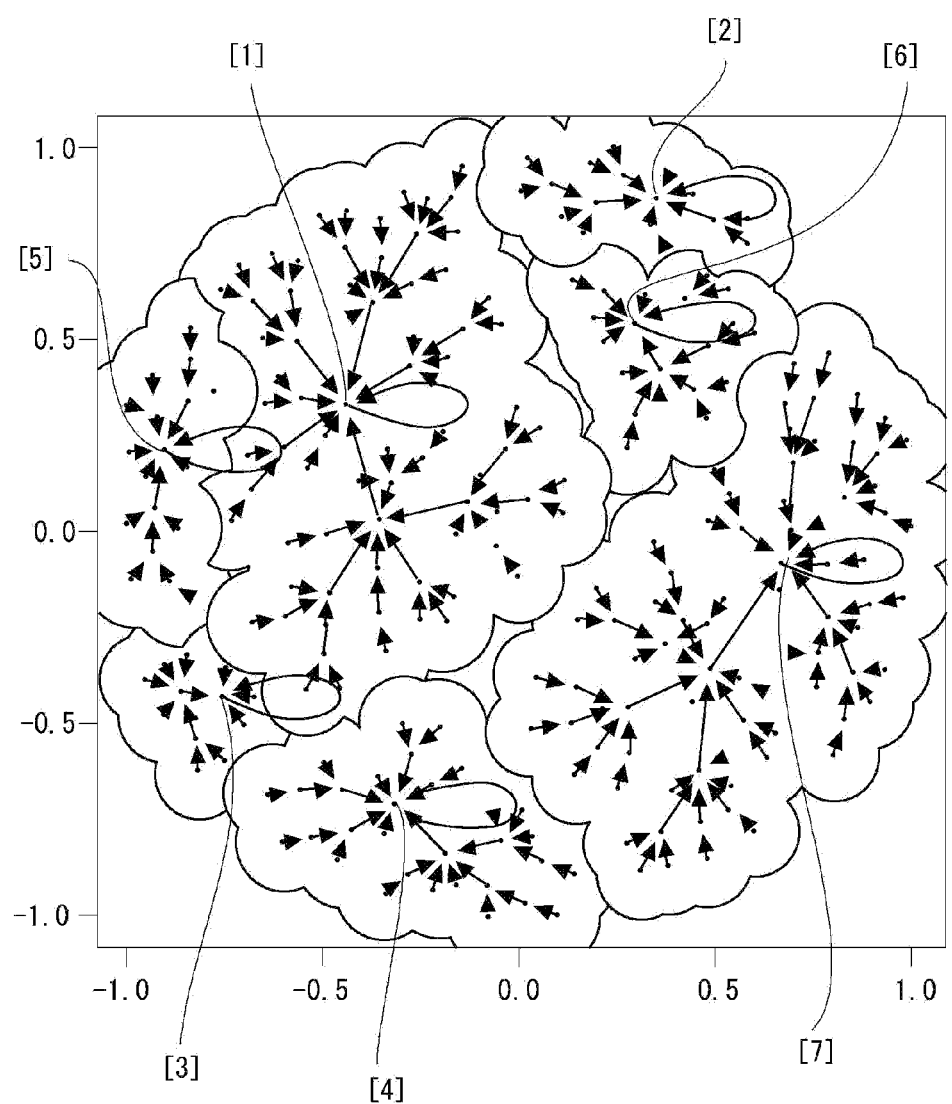
FIG. 8 is a diagram showing an example of attraction regions of basins.
Figure 9:
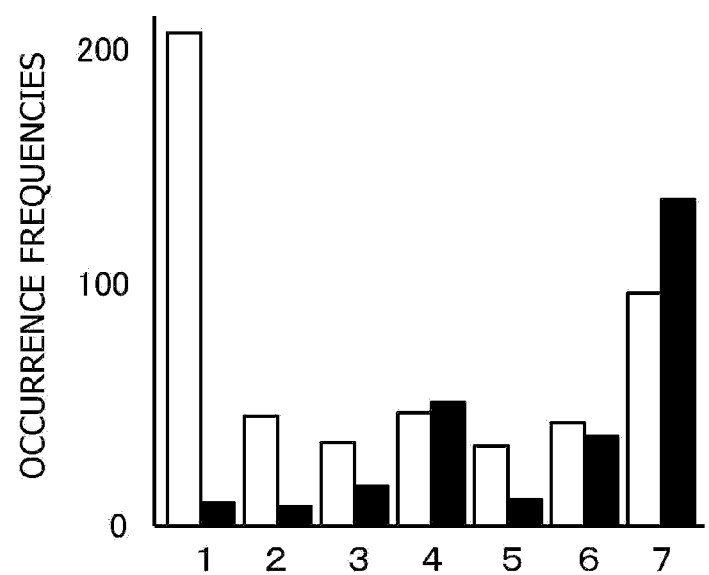
FIG. 9 is a diagram showing an example of the relationship between each region and the onset risk.

FIG. 8 shows the characteristics of the attraction regions of the basins obtained based on the energy landscape of FIG. 7. That is, FIG. 8 shows the range of coordinates corresponding to each basin in which curves extend from different locations in the directions of gradient descent of energy and reach the basin. FIG. 8 also indicates the regions with the numbers of basins corresponding to Basins 1 to 7 in FIG. 6 in square brackets. FIG. 9 shows the onset frequencies determined based on the presence or absence of onset of diabetes within five years of the samples included in the attraction regions. That is, FIG. 9 shows an example of the relationship between the attraction regions and the onset risk, which is an example of the "attribute" according to the present invention. In FIG. 9, the vertical axis represents the number of people, and the horizontal axis represents Basins 1 to 7. The white bar graph on the left represents the number of people who did not develop diabetes, and the black bar graph on the right represents the number of people who developed diabetes. For example, it can be seen that people classified into the attraction regions including Basins 7, 4, and 6 were at high risk of developing diabetes within five years, even though their original states were different. The graph also shows that those who were in the attraction regions including Basins 1 and 2 had a low risk of developing diabetes within five years. It also shows that those who were in the attraction region of Basin 6 were at high risk of developing diabetes within five years, despite the low 2-hour oral glucose tolerance test value.

By binarizing clinical data of a patient of evaluation target who is not one of the samples and obtaining the coordinates of the data in the energy landscape in the same manner as above, it is possible to identify the state of this patient and the state that is likely to transition in the future, based on FIGS. 7 and 8.

The present embodiment creates an energy landscape while maintaining the correspondence with the original samples, allowing for the evaluation of the relationship with each state. The present embodiment also allows the past and current states to be visually recognized. Also, it is possible to identify future possibilities. The above-described technique, which differs from conventional techniques, allows multivariate data on the states of living organisms, such as clinical data, to be used to analyze the states of living organisms, such as the states of patients.

Example 2

Referring to FIGS. 10 to 15, another example is now described. Samples of physical examination results of Japanese people were used to produce an energy landscape showing the risk of developing diabetes. The samples included physical examination data of 34,276 individuals who had undergone annual physical examinations for five years or more, and consisted of a total of 224,461 records. The physical examination data included the following items. The values of the following items were binarized using reference values as the thresholds.

(1) Fasting blood glucose
(2) HbA1c
(3) Urinal sugar
(4) Systolic blood pressure
(5) Abdominal circumference
(6) BMI
(7) ALT (GPT)
(8) γ-GT
(9) Red blood cell count
(10) Hemoglobin content Also, based on the physical examination results and health insurance claims data obtained during the observation period, the samples were classified into diabetes, suspected diabetes (diabetic type), and non-diabetes. The relationship between the state stability and the risk was evaluated based on the classification results. Of the samples, 8,869 people were already diabetic at the start of observation, 13,803 people developed diabetes during the observation period, and 13,000 people did not develop diabetes during the observation period.

Figure 10:
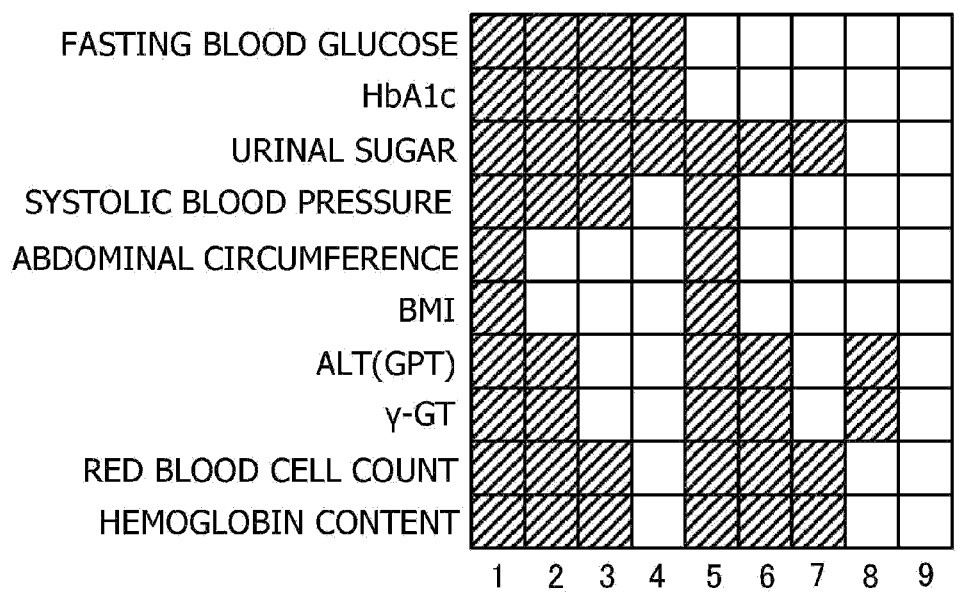
FIG. 10 is a diagram showing an example of combinations of binarized measurement values in stable states.
Figure 11:
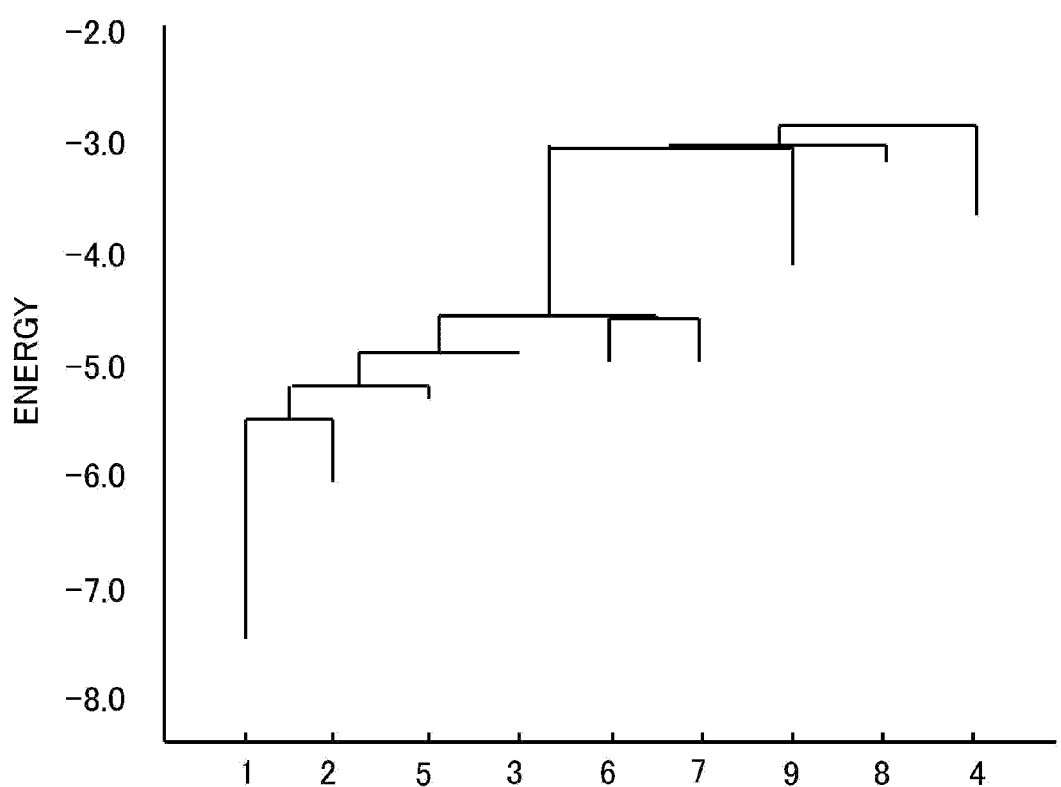
FIG. 11 is an example of a graph showing the levels of energy of basins.

Using combinations of the binarized measurement values of the items described above, the parameters $h_i$ and $J_{ij}$ of the Ising model that fit the occurrence frequencies of combinations were estimated to calculate energies E. Using the energies E thus obtained, the states where the energies E were lower than the surroundings were identified and determined as basins. FIG. 10 shows these basins 1 to 9 corresponding to combinations of binarized values. In the example of FIG. 10, the vertical axis represents the items, fasting blood glucose, HbA1c, urinal sugar, systolic blood pressure, abdominal circumference, BMI, ALT (GPT), γ-GT, red blood cell count, and hemoglobin content from the top. The color of each square indicates the value of the corresponding item. The hatched square represents 0, and the white square represents 1. The horizontal axis represents the nine basins 1 to 9 that were identified as basins. For example, for Basin 1, the values of all items were 0. For Basin 2, only abdominal circumference and BMI had a value of 1. For Basin 3, abdominal circumference, BMI, ALT (GPT), and γ-GT had a value of 1. FIG. 11 is a graph showing the levels of energy of the basins. FIG. 11 is a disconnectivity graph that shows energy levels along the vertical axis and Basins 1 to 9 along the horizontal axis. The nodes at the distal ends of the branches represent basins. The node at a branch point represents the level of energy E at the lowest position along the ridgeline between basins. In addition to the basins, the energy levels can also be obtained from the values of h and J that are estimated based on the frequency of occurrence of the combinations of the values of the above items.

Furthermore, the coordinates corresponding to each state were placed in two-dimensional space using the Fruchterman-Reingold algorithm, and an image was drawn by interpolating the levels of energy E between the coordinates using the Akima algorithm. In case the drawing is difficult because the number of possible combinations of item values is too large, the calculation may be performed using states with energy levels that are lower than a specific energy.

Figure 12:
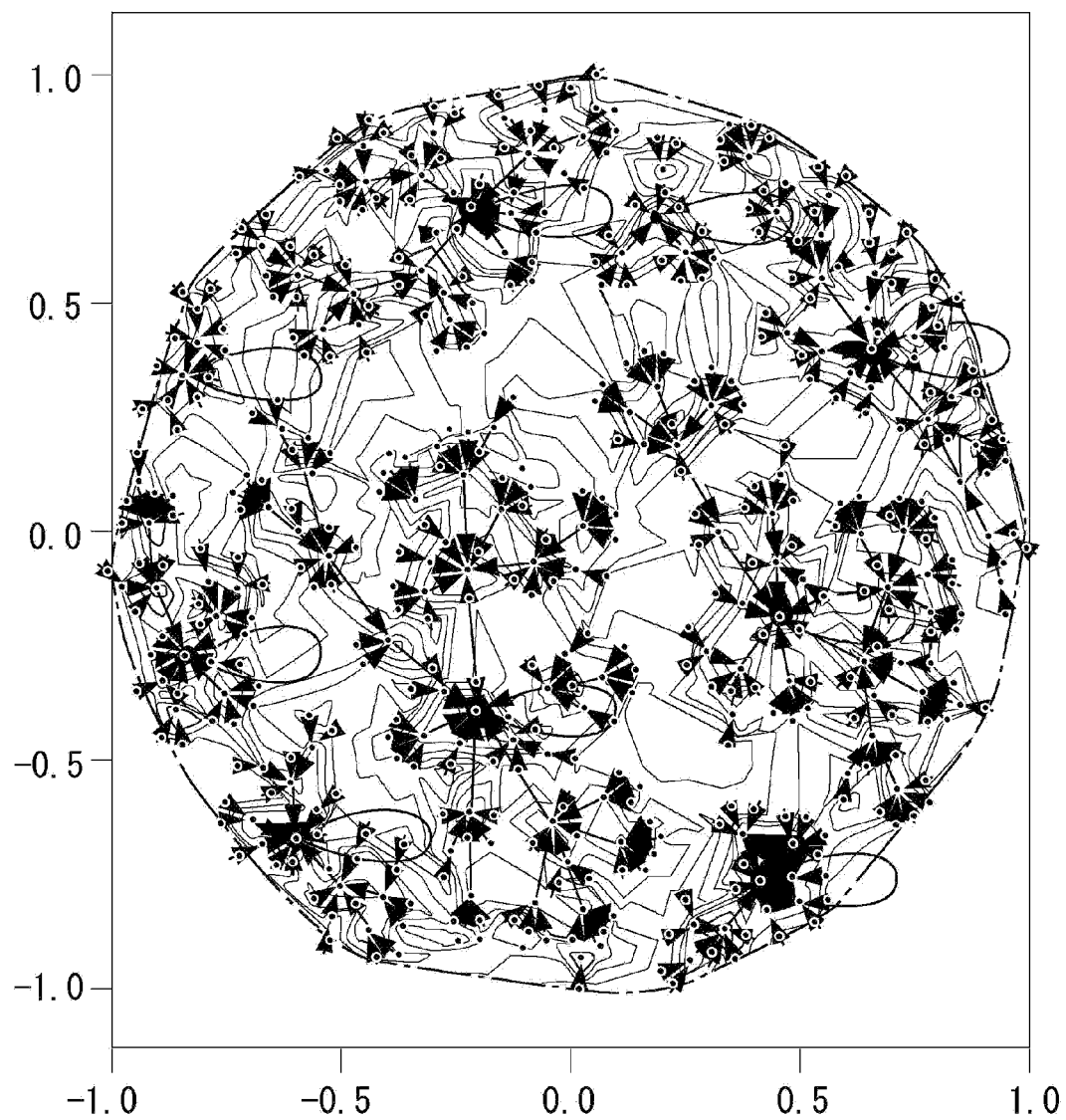
FIG. 12 is an example of an energy landscape showing the levels of energy of states placed in two-dimensional space.

FIG. 12 is an energy landscape in which the levels of energy E of states placed in two-dimensional space are represented by contour lines. Regions in black represent basins and their neighboring regions (valleys). Each arrow indicates a path extending in the direction of gradient descent from the corresponding location. That is, a location where arrows gather is a basin.

Figure 13:
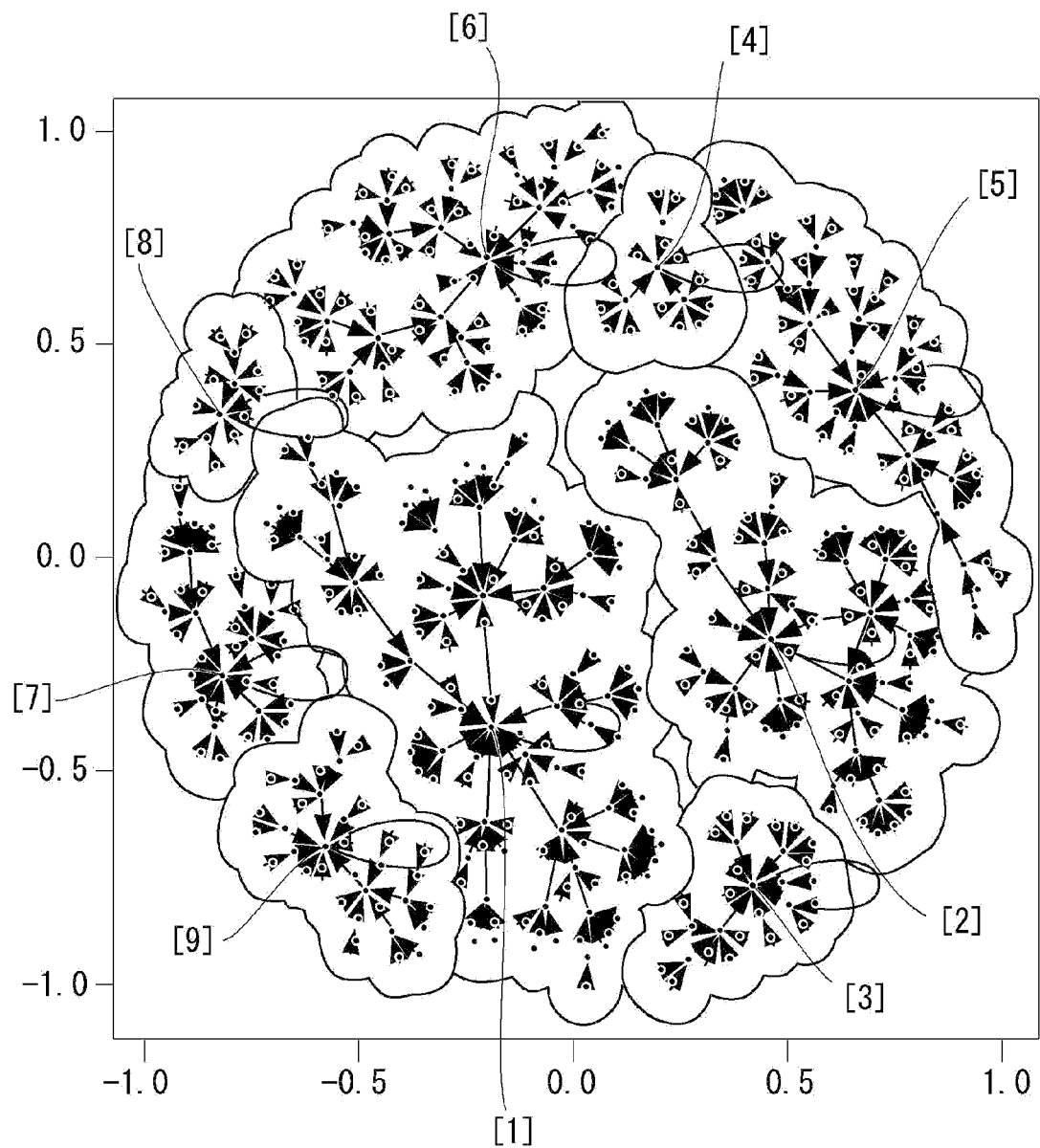
FIG. 13 is a diagram showing an example of attraction regions of basins.
Figure 14:
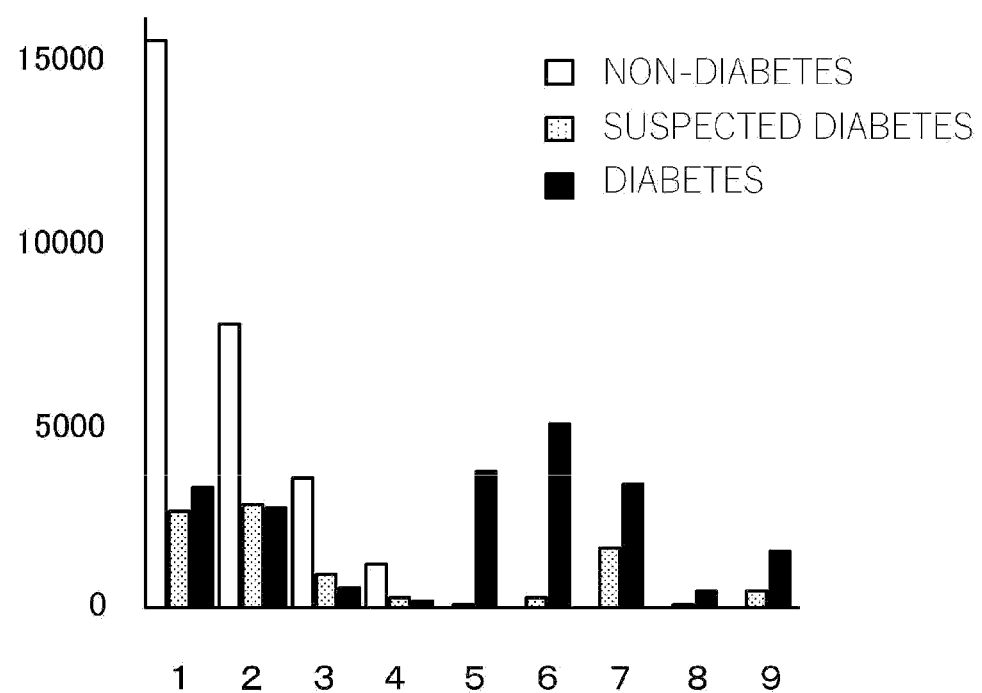
FIG. 14 is a diagram showing an example of the relationship between each region and the onset risk.

FIG. 13 shows the characteristics of the attraction regions of the basins obtained based on the energy landscape of FIG. 12. That is, FIG. 13 shows the range of coordinates corresponding to each basin in which curves extend from different locations in the directions of gradient descent of energy and reach the basin. FIG. 13 also indicates the regions with the numbers of basins corresponding to Basins 1 to 9 in FIG. 10 in square brackets. FIG. 14 shows the onset frequencies determined based on the classification of the samples in the attraction regions into the presence and absence of onset of diabetes and suspected diabetes. That is, FIG. 14 shows an example of the relationship between the attraction regions and the onset risk. In FIG. 14, the vertical axis represents the number of unique individuals who had been in the corresponding attraction region, and the horizontal axis represents Basins 1 to 9. The white bar graph represents the number of people who did not develop diabetes, the gray bar graph represents the number of people with suspected diabetes, and the black bar graph represents the number of people who developed diabetes. For example, it can be seen that many people classified into the attraction regions including Basins 7 and 9 were with suspected diabetes or had developed diabetes, even though their original conditions were different. These attraction regions thus represent a high risk. Many people in the attraction regions including Basins 1 and 2 were non-diabetic at the time of observation, but there were a certain percentage of people with suspected diabetes. Thus, these basins do not necessarily indicate a low risk of developing diabetes. Those in the attraction regions of Basins 8 and 9 had higher urinal sugar as well as higher fasting blood glucose and HbA1c, which are characteristics of diabetes. This indicates a high risk of developing the condition of diabetes.

Figure 15:
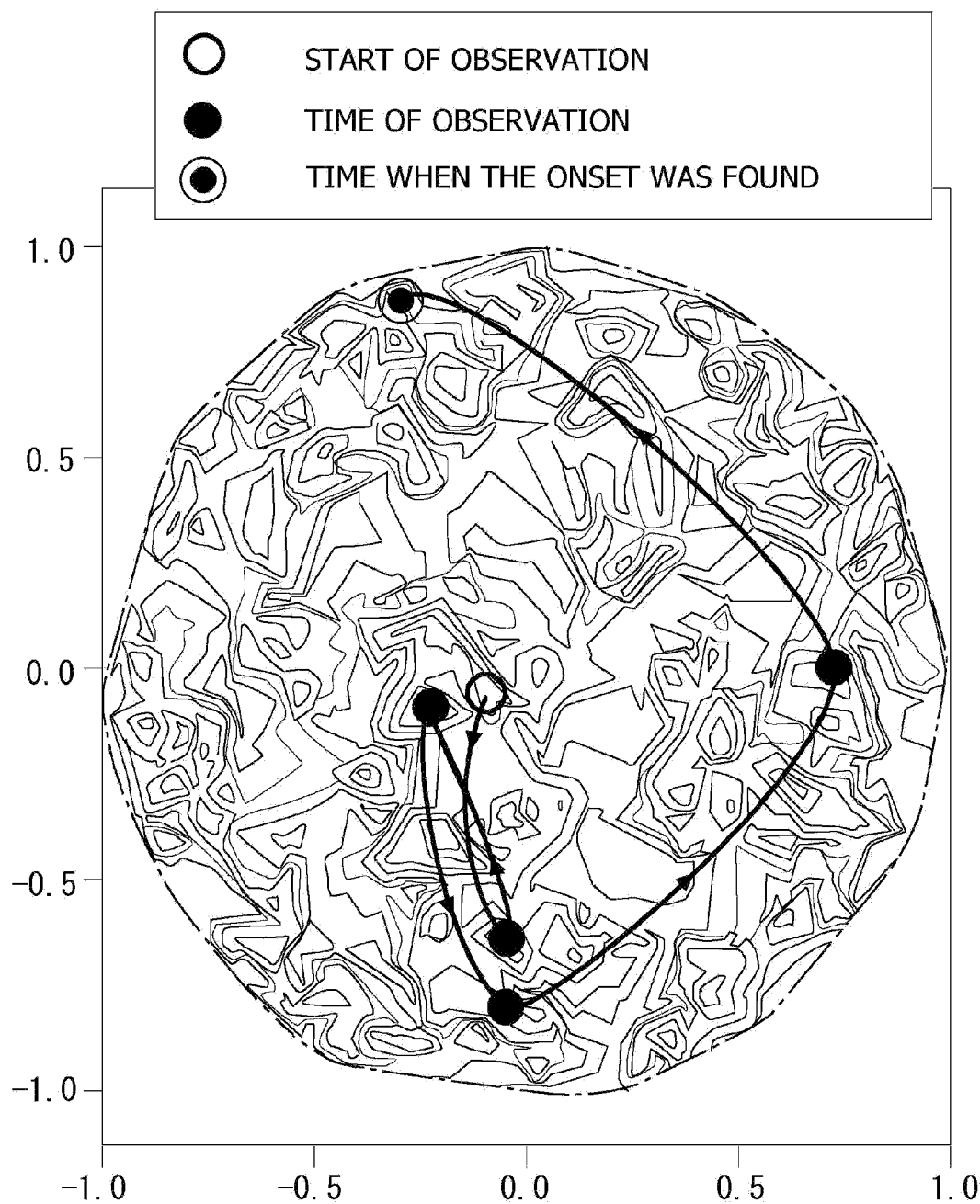
FIG. 15 is a diagram showing an example in which the change of state over time of a physical examinee who developed diabetes during an observation period is superimposed on an energy landscape.

When data is collected continually over time like the above samples, the state transition can be drawn as a trajectory on the energy landscape. FIG. 15 shows the change of state over time of a physical examinee drawn on the energy landscape. This examinee developed diabetes during the observation period. The hollow circle represents the state at the start of observation, each solid circle represents the state at the time of observation, and the double circle represents the state at the time when the onset was found. The graphs show that the state stayed for some time in the attraction region 1 while moving within this region, then transitioned to the attraction region 2, and eventually reached a state included in the attraction region 6 before the onset of diabetes.

By binarizing clinical data and physical examinations data of a patient of evaluation target who is not one of the samples and obtaining the coordinates of the data in the energy landscape in the same manner as above, it is possible to draw a graph that gives a bird's eye view of the time change, like FIG. 15, as well as the graphs of FIGS. 7, 8, 12, and 13, for example. Such graphs allow for the comprehension of the history of states of a patient or physical examinee and the state that is likely to transition in the future.

The examples demonstrate that creating an energy landscape while maintaining the correspondence with the original samples allows for the evaluation of the relationship with each state. Furthermore, as shown in Examples 1 and 2, the items used as the spin variables of the Ising model can be appropriately selected according to the states and the samples to be represented by the energy landscape.

Modifications

The present invention is not limited to the illustrative configurations of the embodiments described above. The present invention is not limited to the energy landscape that is created from clinical data and represents the risk of developing diabetes. The present invention can represent various states of living organisms. For example, answers to questionnaires may be used to create an energy landscape that represents the risk of menopausal disorder. Time-series data on the activity amounts, for example, may be used to create an energy landscape that represents the state of wakefulness and sleep. Data of various measurements of animals may be used to create an energy landscape that represents the states of health or appetitive behavior of animals. An energy landscape may be created that represents the growing state of plants. Furthermore, an energy landscape may be created that represents the state of proliferation, differentiation, and interaction between species of cells and microorganisms.

The present invention includes a computer program that executes the processes described above and a computer-readable storage medium storing the program. The storage medium storing the program can perform the foregoing processes by causing a computer to execute the program.

Here, a computer-readable storage medium may be a storage medium that can store information such as data and programs by electrical, magnetic, optical, mechanical, or chemical action and can be read by a computer. Examples of the storage medium that is removable from a computer include a flexible disk, magneto-optical disk, optical disk, magnetic tape, and memory card. Examples of the storage medium that is fixed to a computer include HDD, solid state drive (SSD), and ROM.

What is claimed is:

1. A state visualization device comprising:
    a coarse-graining portion configured to perform coarse-graining on values corresponding to a plurality of items included in sample data;
    a model creation portion configured to obtain, using binarized values, a mathematical model for calculating energies each fitting a frequency of occurrence of a state represented by a combination of values corresponding to the items;
    a graph creation portion configured to create a graph in which the state is placed in two-dimensional space;
    an interpolation processing portion configured to interpolate energies between the states to create an interpolated graph; and
    an evaluation processing portion configured to binarize data of an evaluation target and determine a position of the data in the interpolated graph;
    wherein an attraction region that is local minimum that the energy arrives on the interpolated graph and a predetermined attribute of the sample data that belongs to the attraction region are associated with each other and stored in a storage device, the evaluation processing portion is configured to extract an attribute corresponding to the data of the evaluation target from the storage device and output the attribute, the interpolated graph is an energy landscape, and the position in the interpolated graph is coordinates in the energy landscape.

2. The state visualization device according to claim 1, wherein the evaluation processing portion is configured to binarize the data of the evaluation target obtained at a plurality of time points, determine a plurality of positions of the data in the interpolated graph, and superimpose and display a course of change, over time, of the positions in the interpolated graph.

3. The state visualization device according to claim 1, wherein the coarse-graining portion is configured to binarize the values corresponding to the plurality of items included in the sample data.

4. A state visualization method to be performed by a computer, the method comprising:

performing coarse-graining on values corresponding to a plurality of items included in sample data;

obtaining, using binarized values, a mathematical model for calculating energies each fitting a frequency of occurrence of a state represented by a combination of values corresponding to the items;

creating a graph in which the state is placed in two-dimensional space;

interpolating energies between the states to create an interpolated graph; and binarizing data of an evaluation target and determining a position of the data in the interpolated graph;

wherein an attraction region that is local minimum that the energy arrives on the interpolated graph and a predetermined attribute of the sample data that belongs to the attraction region are associated with each other and stored in a storage device, extracting an attribute corresponding to the data of the evaluation target from the storage device and outputting the attribute, the interpolated graph is an energy landscape, and the position in the interpolated graph is coordinates in the energy landscape.

5. The state visualization method according to claim 4, wherein the graph represents a state of a living organism or represents a health state of a human, or the graph is used to predict a health state of a human.

6. A non-transitory storage medium storing a state visualization program executable by a computer, the program causing the computer to:

perform coarse-graining on values corresponding to a plurality of items included in sample data;

obtain, using binarized values, a mathematical model for calculating energies each fitting a frequency of occurrence of a state represented by a combination of values corresponding to the items;

create a graph in which the state is placed in two-dimensional space;

interpolate energies between the states to create an interpolated graph; and binarize data of an evaluation target and determine a position of the data in the interpolated graph;

wherein an attraction region that is local minimum that the energy arrives on the interpolated graph and a predetermined attribute of the sample data that belongs to the attraction region are associated with each other and stored in a storage device, extract an attribute corresponding to the data of the evaluation target from the storage device and outputting the attribute, the interpolated graph is an energy landscape, and the position in the interpolated graph is coordinates in the energy landscape.

\* \* \* \* \*